US00PP37454P3

(12) United States Plant Patent
Kievit

(10) Patent No.: US PP37,454 P3
(45) Date of Patent: Jun. 2, 2026

(54) ***SALVIA* PLANT NAMED 'BALSALPUR154'**

(50) Latin Name: *Salvia nemorosa*
Varietal Denomination: Balsalpur154

(71) Applicant: Ball Horticultural Company, West Chicago, IL (US)

(72) Inventor: Christa Kievit, Vessem (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 19/358,171

(22) Filed: Oct. 14, 2025

(65) Prior Publication Data

US 2026/0114348 P1 Apr. 23, 2026

Related U.S. Application Data

(60) Provisional application No. 63/709,357, filed on Oct. 18, 2024.

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 5/02
See application file for complete search history.

*Primary Examiner* — Kent L Bell
(74) *Attorney, Agent, or Firm* — Megan Bowman

(57) ABSTRACT

A new and distinct cultivar of *Salvia* plant named 'Balsalpur154', characterized by its dark, purple-colored flowers, medium, green-colored foliage, and moderately vigorous, compact growth habit, is disclosed.

1 Drawing Sheet

Latin name of genus and species of plant claimed: *Salvia nemorosa.*

Variety denomination: 'Balsalpur154'.

CROSS REFERENCE TO RELATED APPLICATIONS

This application claims the benefit of U.S. Provisional Application No. 63/709,357 filed Oct. 18, 2024.

BACKGROUND OF THE INVENTION

The present invention relates to a new and distinct cultivar of *Salvia* plant botanically known as *Salvia nemorosa* and hereinafter referred to by the cultivar name 'Balsalpur154'.

The new cultivar originated in a controlled breeding program in Hem, the Netherlands during August 2012. The objective of the breeding program was the development of *Salvia* cultivars having large flowers with attractive coloration and a compact growth habit.

The new *Salvia* cultivar is the result of self-pollination of proprietary *Salvia nemorosa* breeding selection L93-1, not patented, characterized by its medium, purple-colored flowers, medium, green-colored foliage and moderate, semi-upright growth habit. The new cultivar was discovered and selected as a single flowering plant within the progeny of the above stated self-pollination during July 2013 in a controlled environment in Hem, the Netherlands.

Asexual reproduction of the new cultivar by terminal stem cuttings since July 2013 in Hem, the Netherlands and West Chicago, Illinois has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balsalpur154' as a new and distinct cultivar of *Salvia* plant:

1. Dark purple-colored flowers;
2. Medium, green-colored foliage; and
3. Moderately vigorous, compact growth habit.

Plants of the new cultivar differ from plants of the female parent primarily in having darker, purple-colored flowers and a more compact growth habit.

Of the many commercially available *Salvia* cultivars, the most similar in comparison to the new cultivar is *Salvia* LYRICAL Blues, 'Balyriclu', U.S. Plant Pat. No. 22,919. However, in side-by-side comparisons, plants of the new cultivar differ from plants of 'Balyriclu' in at least the following characteristics:

1. Plants of the new cultivar have larger flowers with more blue coloration than plants of 'Balyriclu'; and
2. Plants of the new cultivar have a more compact growth habit than plants of 'Balyriclu'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balsalpur154'. The plants were approximately 11 months old and grown in 4-inch pots for approximately 8 weeks in a greenhouse in West Chicago, Illinois.

DETAILED BOTANICAL DESCRIPTION

Figure 1:
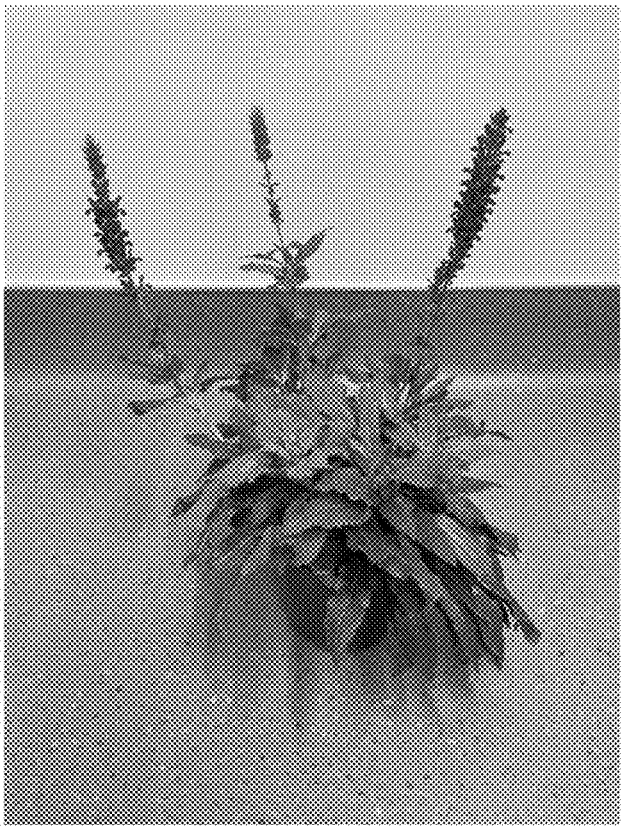
FIG. 1 illustrates a side view of the overall growth and flowering habit of 'Balsalpur154'.
Figure 2:
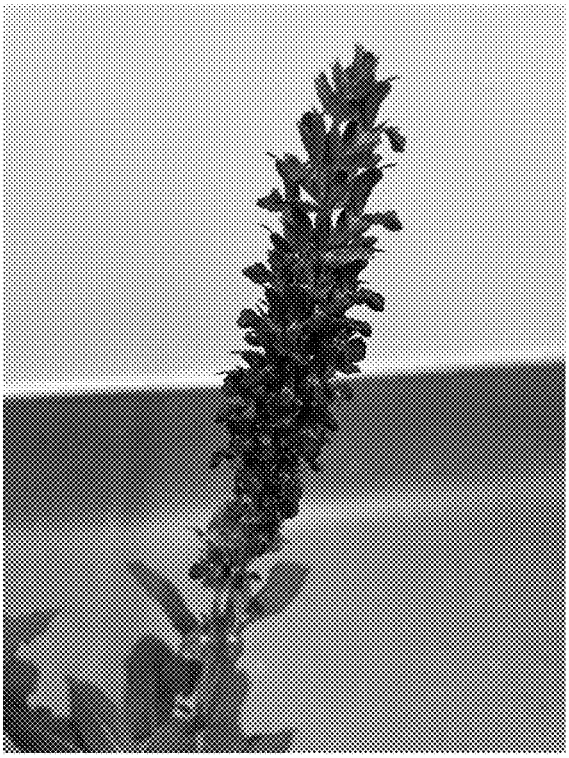
FIG. 2 illustrates a close-up view of an inflorescence of 'Balsalpur154'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in December 2024 under natural light conditions in West Chicago, Illinois.

The following descriptions and measurements describe approximately 11-month-old plants produced from cuttings from stock plants and grown in a double polyethylene greenhouse under conditions comparable to those used in commercial practice. The plants were grown in West Chicago, Illinois in 4-inch pots for approximately 8 weeks utilizing a soilless growth medium. Plants were not pinched prior to transplant. Greenhouse temperatures were maintained at approximately 60° F. to 65° F. (15.6° C. to 18.3° C.) during the day and approximately 55° F. to 60° F. (12.8° C. to 15.6° C.) during the night. Supplemental lighting was used. Measurements and numerical values represent averages of typical plants.

Botanical classification: *Salvia nemorosa* 'Balsalpur154'.

Parentage:

*Female parent*.—Proprietary *Salvia nemorosa* breeding selection L93-1, not patented.

Propagation:

*Type cutting*.—Terminal stem.

*Time to initiate roots*.—Approximately 6 to 9 days.

*Time to produce a rooted cutting*.—Approximately 21 to 28 days.

*Root description*.—Medium thickness, fibrous, brown in color.

*Rooting habit*.—Freely branching.

Plant description:

*Commercial crop time*.—Approximately 10 to 12 weeks from a rooted cutting to finish in a 15 cm pot.

*Growth habit and general appearance*.—Moderately vigorous, compact growth habit.

*Hardiness*.—USDA Zone 5a.

*Size*.—Height from soil level to top of plant plane: Approximately 25.0 cm. Width: Approximately 21.0 cm.

*Branching habit*.—Freely branching. Pinching enhances lateral branching. Quantity of branches per plant: Approximately 2 main basal branches and approximately 14 lateral branches.

*Branch*.—Shape: Square in cross section. Strength: Strong. Length to base of inflorescence: Approximately 28.0 cm. Diameter: Approximately 6.0 mm. Length of central internode: Approximately 6.0 cm. Texture: Moderately pubescent. Color of young and mature stems: 143A.

Foliage description:

*General Description*.—Quantity of leaves per main branch: Approximately 12. Fragrance: Light, sage-like. Form: Simple. Arrangement: Opposite.

*Leaves*.—Aspect: Acute to perpendicular angle to stem. Shape: Ovate to deltoid. Margin: Crenate. Apex: Acute. Base: Truncate to slightly oblique. Venation pattern: Pinnate. Length of mature leaf: Approximately 6.0 cm. Width of mature leaf: Approximately 2.5 cm. Texture of upper surface: Rugose, sparsely pubescent. Texture of lower surface: Rugose, densely pubescent. Color of upper surface of young foliage: 137C and venation of 147B. Color of lower surface of young foliage: Closest to 137D with venation of 145C. Color of upper surface of mature foliage: 138A and venation of 147B. Color of lower surface of mature foliage: 137D with venation of 146C.

*Petiole*.—Length: Approximately 4.5 cm. Diameter: Approximately 4.0 mm. Texture: Moderately pubescent. Color: 146B.

Flowering description:

*Flowering habit*.—'Balsalpur154' is freely flowering under outdoor growing conditions with substantially continuous blooming from spring through autumn and year-round in greenhouse environment.

*Lastingness of individual floret*.—Approximately 4 to 5 days.

Inflorescence description:

*General description*.—Type: Spikes in verticillaster arrangement, florets in clusters of five, not persistent. Quantity of inflorescences per plant: Approximately 3. Fragrance: Faint, sweet. Length or height of inflorescence: Approximately 20.0 cm. Width of inflorescence: Approximately 2.5 cm. Quantity of fully open flowers per inflorescence: Approximately 20.

*Peduncle*.—Shape: Square in cross section. Strength: Strong. Aspect: Erect. Length: Approximately 5.5 cm. Diameter: Approximately 4.0 mm. Texture: Densely glandular pubescent. Color: N144B.

Flower description:

*Type*.—Single, zygomorphic.

*Bud*.—Rate of opening: Generally, takes 2 to 3 days for bud to progress from first color to fully open flower.

*Bud just before opening*.—Shape: Obovoid. Length: Approximately 0.8 cm. Diameter: Approximately 3.0 mm. Texture: Moderately pubescent. Color: Calyx of N92A and petals of N92C.

*Corolla*.—Shape: Bilabiate, lower lip having three lobes, base fused. Width: Approximately 0.5 cm. Length: Approximately 1.2 cm. Depth: Approximately 1.0 cm.

*Upper lip*.—Shape: Hooded. Margin: Entire. Apex: Rounded. Length from throat: Approximately 1.0 cm. Width: Approximately 3.0 mm. Texture of inner surface: Glabrous. Texture of outer surface: Moderately pubescent. Color of inner surface when first and fully open: 86A. Color of outer surface when first and fully open: N88A.

*Lower lip*.—Shape of central lobes: Oblong. Margin: Entire. Apex of central lobe: Emarginate. Apex of lateral lobes: Rounded. Length from throat of central lobe: Approximately 0.6 cm. Width of central lobe: Approximately 5.0 mm. Length from throat of lateral lobes: Approximately 0.3 cm. Width of lateral lobes: Approximately 0.5 mm. Texture of upper surface: Glabrous. Texture of lower surface: Glabrous. Color of upper surface when first and fully open: 86A Color of lower surface when first and fully open: N88A.

*Corolla tube*.—Length: Approximately 1.0 cm. Diameter at opening: Approximately 3.0 mm. Diameter at base: Approximately 2.0 mm. Texture of inner and outer surfaces: Glabrous. Color of inner surface when first and fully open: 76D. Color of outer surface when first and fully open: 76D.

*Calyx*.—Shape: Tubular. Length: Approximately 1.0 cm. Diameter: Approximately 2.0 mm.

*Sepals*.—Quantity per flower: Three, Fused into two lobes. Shape: Obovate. Apex: Upper lobe bifurcate, lower lobe notched. Length: Approximately 1.0 cm. Width of lobes: Approximately 3.0 mm. Texture of inner and outer surfaces: Moderately pubescent. Color of inner surface: 143B with tips of N92D. Color of outer surface: 141C with tips of N92D.

*Bracts*.—Quantity: One bract located at the base of floret cluster. Shape: Ovate. Apex: Acuminate. Length: Approximately 0.7 cm. Width: Approximately 6.0 mm. Texture of inner surface: Glabrous. Texture of outer surface: Moderately pubescent. Color of inner surface: NN155D with an overlay of about NN78C and 135A. Color of outer surface: NN78C and 135A.

*Pedicel*.—Strength: Strong, flexible. Aspect: At an acute angle. Length: Approximately 1.0 mm. Diameter: Approximately 1.0 mm. Texture: Densely pubescent. Color: 146B.

*Reproductive organs*.—Androecium: Stamen quantity: 2 per flower, dorsifixed, strongly curved. Stamen length: Approximately 0.7 cm. Filament length: Approximately 0.5 cm. Filament color: NN 155D with lower half of 86A. Anther shape: Oblong. Anther length: Approximately 2.0 mm. Anther color: N92C. Pollen amount: Abundant. Pollen color: 14A. Gynoecium: Pistil quantity: 1 per flower, slightly curved. Pistil length: Approximately 2.3 cm. Stigma shape: Cleft, two-parted. Stigma length: 3.4 mm. Stigma color: 86A. Style length: Approximately 3.0 cm. Style color: 91D. Style texture: Glabrous. Ovary length: Approximately 1.0 mm. Ovary color: 11A.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Balsalpur154', substantially as herein illustrated and described.

* * * * *